(12) United States Patent
Shanley et al.

(10) Patent No.: US 9,498,358 B2
(45) Date of Patent: Nov. 22, 2016

(54) IMPLANTABLE MEDICAL DEVICE WITH OPENINGS FOR DELIVERY OF BENEFICIAL AGENTS WITH COMBINATION RELEASE KINETICS

(75) Inventors: John F. Shanley, Redwood City, CA (US); Theodore L. Parker, Danvile, CA (US); Thai Minh Nguyen, Santa Clara, CA (US); Micheline Lisa Markey, Atherton, CA (US); Gary W. Steese-Bradley, San Jose, CA (US)

(73) Assignee: Innovational Holdings LLC, Irvine, CA (US)

( * ) Notice: Subject to any disclaimer, the term of this patent is extended or adjusted under 35 U.S.C. 154(b) by 1572 days.

(21) Appl. No.: 11/448,319

(22) Filed: Jun. 6, 2006

(65) Prior Publication Data

US 2006/0229713 A1 Oct. 12, 2006

Related U.S. Application Data

(63) Continuation-in-part of application No. 10/668,430, filed on Sep. 22, 2003, now abandoned.

(60) Provisional application No. 60/412,489, filed on Sep. 20, 2002, provisional application No. 60/688,191, filed on Jun. 6, 2005.

(51) Int. Cl.
*A61F 2/06* (2013.01)
*A61F 2/915* (2013.01)
*A61F 2/91* (2013.01)

(52) U.S. Cl.
CPC ............... *A61F 2/915* (2013.01); *A61F 2/91* (2013.01); *A61F 2002/91541* (2013.01); *A61F 2002/91558* (2013.01); *A61F 2210/0004* (2013.01); *A61F 2250/0035* (2013.01); *A61F 2250/0068* (2013.01)

(58) Field of Classification Search
CPC ............. A61F 2/91; A61F 2250/0035; A61F 2250/0068
USPC ........................ 623/1.11, 1.42, 1.39; 424/423
See application file for complete search history.

(56) References Cited

U.S. PATENT DOCUMENTS

| | | | |
|---|---|---|---|
| 4,733,665 A | 3/1988 | Palmaz | |
| 4,739,762 A | 4/1988 | Palmaz | |
| 4,776,337 A | 10/1988 | Palmaz | |
| 4,969,458 A | 11/1990 | Wiktor | |
| 5,716,981 A | 2/1998 | Hunter et al. | |
| 6,241,762 B1 | 6/2001 | Shanley | |

(Continued)

FOREIGN PATENT DOCUMENTS

| | | |
|---|---|---|
| WO | 03047463 | 6/2003 |
| WO | 2005016396 | 2/2005 |

OTHER PUBLICATIONS

European Office Action issued in the corresponding European Application No. 06 772 340.3, dated Aug. 28, 2015, 6 pages.

*Primary Examiner* — Diane Yabut
(74) *Attorney, Agent, or Firm* — Hamre, Schumann, Mueller & Larson, P.C.

(57) ABSTRACT

A method and system for delivering drug includes a first set of holes filled with a first formulation of the drug and a second set of holes filled with a second formulation of the same drug. This dual formulation or dual release kinetic system allows the creation of specifically tailored release kinetics by summation of multiple release kinetics.

18 Claims, 5 Drawing Sheets

(56) References Cited

U.S. PATENT DOCUMENTS

| | | |
|---|---|---|
| 6,562,065 B1 | 5/2003 | Shanley |
| 6,616,765 B1 * | 9/2003 | Wu et al. ............. A61L 31/10 118/320 |
| 6,699,281 B2 * | 3/2004 | Vallana et al. ............. 623/1.42 |
| 2001/0038863 A1 * | 11/2001 | Jaenicke et al. ............. 424/725 |
| 2002/0007209 A1 * | 1/2002 | Scheerder et al. ............. 623/1.15 |
| 2002/0082680 A1 * | 6/2002 | Shanley et al. ............. 623/1.16 |
| 2003/0082680 A1 | 5/2003 | Hostetter et al. |
| 2003/0181973 A1 * | 9/2003 | Sahota ............. 623/1.15 |
| 2004/0022824 A1 * | 2/2004 | Li et al. ............. 424/423 |
| 2004/0073294 A1 | 4/2004 | Diaz et al. |
| 2004/0166140 A1 * | 8/2004 | Santini et al. ............. 424/424 |
| 2004/0254635 A1 | 12/2004 | Shanley et al. |
| 2005/0021757 A1 | 1/2005 | Helliwell |
| 2005/0058684 A1 | 3/2005 | Shanley et al. |
| 2005/0100577 A1 | 5/2005 | Parker et al. |
| 2005/0100582 A1 | 5/2005 | Stenzel |
| 2006/0155370 A1 * | 7/2006 | Brister ............. A61F 2/86 623/1.46 |

\* cited by examiner

IMPLANTABLE MEDICAL DEVICE WITH OPENINGS FOR DELIVERY OF BENEFICIAL AGENTS WITH COMBINATION RELEASE KINETICS

This is a continuation-in-part of U.S. patent application Ser. No. 10/668,430, filed on Sep. 22, 2003, now abandoned which claims priority to Provisional Patent Application No. 60/412,489, filed on Sep. 20, 2002, both of which are incorporated herein by reference in their entirety. This application also claims priority to Provisional Patent Application No. 60/688,191 filed on Jun. 6, 2005, which is incorporated herein by reference in its entirety.

BACKGROUND OF THE INVENTION

Field of the Invention

The present invention relates to implantable medical devices, and more particularly to stents that are implanted within a bodily lumen of a living animal or human to support the lumen and maintain patency, and that have openings containing a drug for delivery to the body.

Summary of the Related Art

In the past, permanent or biodegradable devices have been developed for implantation within a body passageway to maintain patency of the passageway. These devices are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as, stainless steel, gold, silver, tantalum, titanium, and shape memory alloys, such as Nitinol.

U.S. Pat. No. 6,241,762 which is incorporated herein by reference in its entirety discloses a non-prismatic stent design which remedies several performance deficiencies of previous stents. In addition, preferred embodiments of this patent provide a stent with large, non-deforming strut and link elements, which can contain holes without compromising the mechanical properties of the strut or link elements, or the device as a whole. Further, these holes may serve as large, protected reservoirs for delivering various beneficial agents to the device implantation site without the need for a surface coating on the stent.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition and vascular smooth muscle cell proliferation and which may ultimately result in renarrowing or even reocclusion of the lumen. Despite the introduction of improved surgical techniques, devices and pharmaceutical agents, the overall restenosis rate for bare metal stents is still reported in the range of 25% to 50% within six to twelve months after an angioplasty procedure. To treat this condition, additional revascularization procedures are frequently required, thereby increasing trauma and risk to the patient.

Conventional stents with surface coatings of various beneficial agents have shown promising results in reducing restenosis. U.S. Pat. No. 5,716,981, for example, discloses a stent that is surface-coated with a composition comprising a polymer carrier and paclitaxel (a well-known compound that is commonly used in the treatment of cancerous tumors). The patent offers detailed descriptions of methods for coating stent surfaces, such as spraying and dipping, as well as the desired character of the coating itself: it should "coat the stent smoothly and evenly" and "provide a uniform, predictable, prolonged release of the anti-angiogenic factor." Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue. The resulting cumulative drug release profile is characterized by a large initial burst, followed by a rapid approach to an asymptote, rather than the desired "uniform, prolonged release," or linear release.

Increasing the thickness of the surface coating has the beneficial effects of improving drug release kinetics including the ability to better control drug release and to allow increased drug loading. However, the increased coating thickness results in increased overall thickness of the stent wall. This is undesirable for a number of reasons, including difficulty in placing the stent in tight lesions, increased trauma to the vessel lumen during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, durations, and the like that can be achieved.

The filled hole or reservoir technology described in U.S. Publication No. 2003/0082680, filed Sep. 7, 2001, and U.S. Publication No. 2004/0073294, filed May 28, 2003, provide a solution to the problem of controlling release kinetics from a stent. The reservoirs allow the deposition of multiple deposits of different polymer only and drug/polymer to achieve a wide variety of release kinetics which cannot be achieved from a surface coating.

Human clinical trials of drug eluting stents have shown that not only is the dose important to the clinical outcome, but the release rate and the increase or decrease in the release rate (the release kinetics) is important in to the clinical outcome. When the release kinetic can be specifically tailored to the biological processes addressed by the stent (i.e. restenosis, inflammation, acute myocardial infarction) the clinical outcome is expected to be improved.

SUMMARY OF THE INVENTION

An implantable medical device, such as a stent, is described having a combination release profile for a drug achieved by the summation of two independent release profiles from two different sets of reservoirs in the device.

In accordance with one aspect of the invention, a medical device for delivery of a therapeutic agent with a combined release profile is comprised of an implantable medical device, a first plurality of openings formed in the implantable medical device containing a first beneficial agent for delivery to tissue, wherein the first beneficial agent comprises a therapeutic agent and a first matrix. The therapeutic agent and first matrix are arranged to deliver the therapeutic agent from the first plurality of openings according to a first release curve. A second plurality of openings are formed in the implantable medical device containing a second beneficial agent for delivery to tissue. The second beneficial agent comprises the therapeutic agent and a second matrix, wherein the therapeutic agent and second matrix are arranged to deliver the therapeutic agent from the second plurality of openings according to a second release curve which is substantially different from the first release curve. The first and second openings together create a combination release kinetic.

In accordance with another aspect of the invention, a method of reducing restenosis in a body passageway comprises the steps of positioning a stent in a body passageway to support the tissue and delivering a therapeutic agent to tissue adjacent the stent to treat restenosis. The stent contains a therapeutic agent in openings in the stent, wherein the therapeutic agent is contained in different openings in the device in at least two different matrices to achieve a combination release kinetic In accordance with a further aspect of the invention, a method of treating acute myocardial infarction comprises the steps of positioning a stent in a blood vessel and delivering the therapeutic agent to blood stream to improve the functioning of the myocardium. The stent contains a therapeutic agent in openings in the device, wherein the therapeutic agent is contained in different openings in the stent in at least two different matrices to achieve a combination release kinetic and delivering the therapeutic agent to blood stream to improve the functioning of the myocardium.

In accordance with yet a further aspect of the invention, an implantable stent is comprised of an expandable stent structure, a plurality of through holes in the stent structure, a biodegradable polymer matrix with drug within the plurality of holes, wherein the same drug with different release kinetics is positioned in different holes.

BRIEF DESCRIPTION OF THE DRAWINGS

The invention will now be described in greater detail with reference to the preferred embodiments illustrated in the accompanying drawings, in which like elements bear like reference numerals, and wherein.

DETAILED DESCRIPTION OF EXEMPLARY EMBODIMENTS

Definitions

Figure 1:
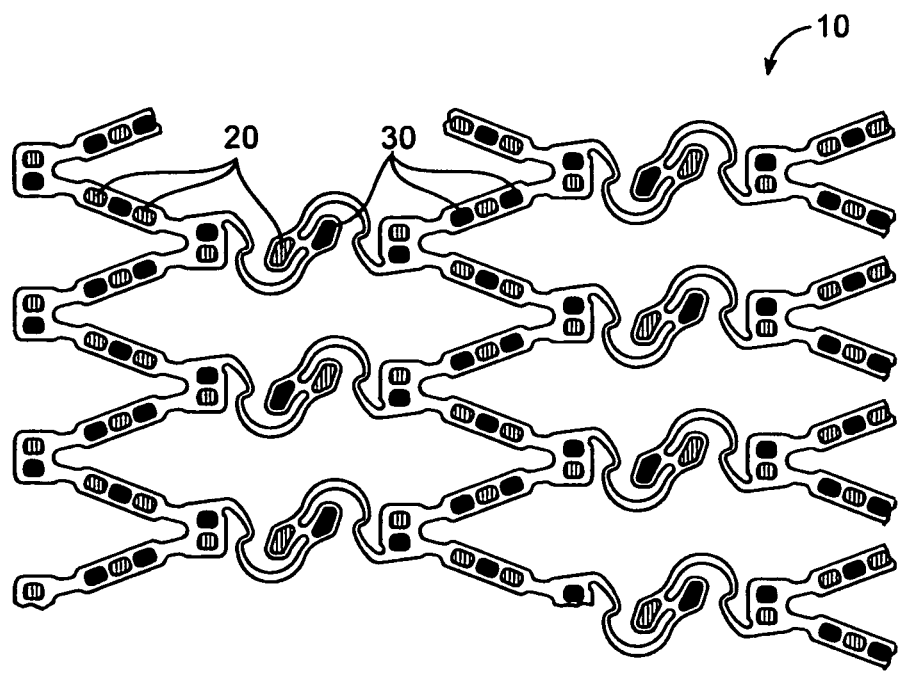
FIG. 1 is an enlarged side view of a portion of an expandable medical device with alternating openings loaded with two different formulations of the same therapeutic agent to achieve a combination release kinetic.

The terms "agent" or "beneficial agent" as used herein are intended to have the broadest possible interpretation and are used to include any therapeutic agent or drug, as well as inactive agents such as barrier layers, carrier layers, therapeutic layers, or protective layers.

The terms "drug" and "therapeutic agent" are used interchangeably to refer to any therapeutically active substance that is delivered to a bodily lumen of a living being to produce a desired, usually beneficial, effect. Beneficial agents may include one or more drug or therapeutic agent.

The present invention is particularly well suited for the delivery of antineoplastics, antiangiogenics, angiogenic factors, anti-inflammatories, immuno-suppressants, antirestenotics, antiplatelet agents, vasodilators, anti-thrombotics, antiproliferatives, such as paclitaxel and Rapamycin, for example, and antithrombins, such as heparin, for example.

The term "erosion" means the process by which components of a medium or matrix are bioresorbed and/or degraded and/or broken down by chemical or physical processes. For example in reference to biodegradable polymer matrices, erosion can occur by cleavage or hydrolysis of the polymer chains, thereby increasing the solubility of the matrix and suspended beneficial agents.

The term "erosion rate" is a measure of the amount of time it takes for the erosion process to occur, usually reported in unit-area per unit-time.

The terms "matrix" or "bioresorbable matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a beneficial agent, as defined herein. A matrix is also a medium that may simply provide support, structural integrity or structural barriers. The matrix may be polymeric, non-polymeric, hydrophobic, hydrophilic, lipophilic, amphiphilic, and the like.

The term "openings" includes both through openings and recesses.

The term "pharmaceutically acceptable" refers to the characteristic of being non-toxic to a host or patient and suitable for maintaining the stability of a beneficial agent and allowing the delivery of the beneficial agent to target cells or tissue.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semi-synthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000. Examples of polymers include but are not limited to, poly-α-hydroxy acid esters such as, polylactic acid (PLLA or DLPLA), polyglycolic acid, polylactic-co-glycolic acid (PLGA), polylactic acid-co-caprolactone; poly (block-ethylene oxide-block-lactide-co-glycolide) polymers (PEO-block-PLGA and PEO-block-PLGA-block-PEO); polyethylene glycol and polyethylene oxide, poly (block-ethylene oxide-block-propylene oxide-block-ethylene oxide); polyvinyl pyrrolidone; polyorthoesters; polysaccharides and polysaccharide derivatives such as polyhyaluronic acid, poly (glucose), polyalginic acid, chitin, chitosan, chitosan derivatives, cellulose, methyl cellulose, hydroxyethylcellulose, hydroxypropylcellulose, carboxymethylcellulose, cyclodextrins and substituted cyclodextrins, such as beta-cyclodextrin sulfobutyl ethers; polypeptides and proteins, such as polylysine, polyglutamic acid, albumin; polyanhydrides; polyhydroxy alkonoates such as polyhydroxy valerate, polyhydroxy butyrate, and the like.

The term "primarily" with respect to directional delivery, refers to an amount greater than about 50% of the total amount of therapeutic agent provided to a blood vessel is provided in the primary direction.

The term "release rate" refers to a measure of the amount of a drug or agent per unit time delivered from a medical device.

The term "release kinetics" refers to the shape of a curve of a plot of an amount of drug or agent delivered over time from a medical device.

The various embodiments of the invention described herein provide different beneficial agents in different openings in the expandable device or beneficial agent in some openings and not in others. The particular structure of the expandable medical device may be varied without departing from the invention. Since each opening is filled independently, individual chemical compositions and pharmacokinetic properties can be imparted to the beneficial agent in each opening to get a desired release kinetic.

One example of the use of different beneficial agents in different openings in an expandable medical device or beneficial agents in some openings and not in others, is in addressing edge effect restenosis. Current generation coated stents have a problem with edge effect restenosis or restenosis occurring just beyond the edges of the stent and progressing around the stent and into the interior luminal space. A change in the release kinetic of the drug at the ends of the stent can address this problem.

FIG. 1 illustrates an expandable medical device 10 having a plurality of holes 20 and 30 containing a beneficial agent for delivery to tissue by the expandable medical device. The expandable medical device 10 shown in FIG. 1 is formed, e.g., cut, from a tube of material to form a cylindrical expandable device. The expandable medical device 10 is described in detail in U.S. Pat. No. 6,562,065 and U.S. Patent Application Publication No. 2005-0261757, each of which are incorporated herein by reference in their entirety.

In the embodiment of FIG. 1, each of the holes 20 are filled with a first formulation of a drug while each of the holes 30 are filled with a second formulation of the same drug. This dual formulation, or dual release kinetic system allows the creation of specifically tailored release kinetics by summation of multiple release kinetics. The combined release kinetics achieved by a combination system, such as that shown in FIG. 1, allow the creation of more complex or refined release kinetics with all types of drugs. The use of summation can achieve previously difficult release kinetics, such as a burst followed by a linear release, a slow linear release and a late burst, or a pulsate release. The present invention is not limited to a combination of first and second formulations positioned in first and second sets of holes in an implantable medical device, and extends to any number of combinations, up to and including having a different formulation positioned in each hole of an implantable medical device. Thus, while exemplary embodiments described herein detail a two-formulation, two-hole-set configuration, three-, four-, and higher order configurations are also aspects of the present invention. A second drug can also be added within the first and second holes or in other holes.

The holes 20 and 30 are advantageously filled by a process of depositing a drug/polymer/solvent solution and evaporating the solvent. This depositing process is continued with various combinations of drug/polymer/solvent and polymer/solvent to lay several sequential deposits within the openings. Together these deposits form an inlay with a release profile determined based on the characteristics, amounts, and sequence of the deposits. Often variation of a polymer only base or cap layer can be used to adequately control the release to a desired release kinetic. Variation of the polymers themselves can also be used to change the release kinetics. However, when these methods don't achieve the release desired, the method described herein with different formulations of the same drug in different holes can be used. The specific release can be further controlled by changing the percentage of holes filled with each of the formulations, as will be seen in the examples which follow.

A further description of one example of the manner in which the beneficial agent may be loaded within the openings 20 and 30 is described in U.S. patent application Ser. No. 10/447,587, filed May 28, 2003, published as U.S. patent application publication no. 2004/0073294 A1 on 15 Apr. 2004, which is incorporated herein by reference in its entirety.

Figure 6:
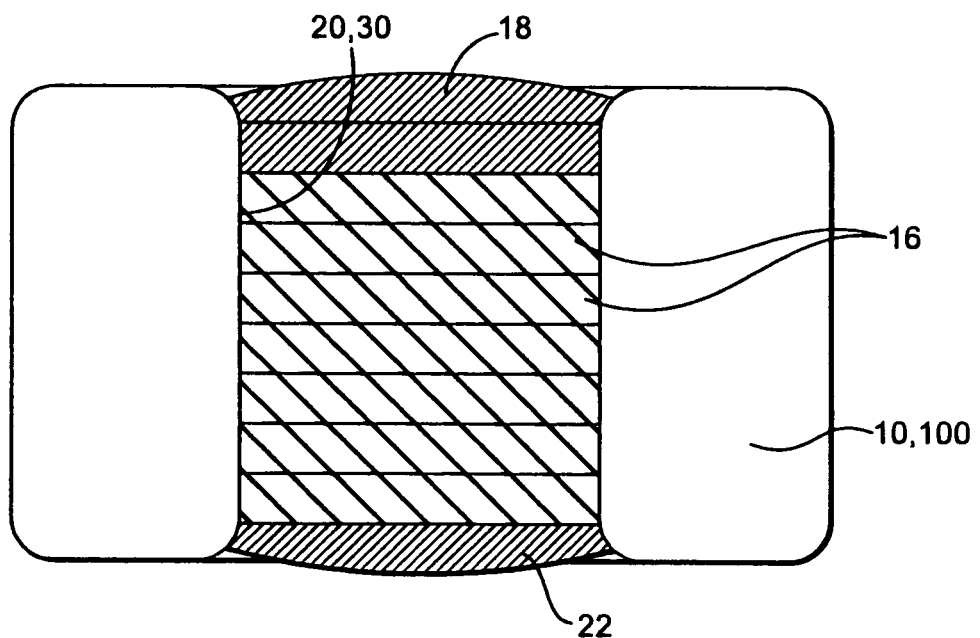
FIG. 6 is an enlarged cross-sectional view of an exemplary lay-up of materials within the opening of a stent embodying principles of the present invention.

FIG. 6 illustrates an enlarged cross-sectional view of an opening or hole 20, 30 of a stent 10, 100. Another aspect of the present invention includes that the stent holes 20, 30 include a drug matrix 16, a cap 18, and a base 22, which each occupy a volume less than the entire volume of the hole When the total volume percentages of the drug matrix 16, cap 18, and base 22 together, relative to the volume of the hole 14, is less than 100%, the hole is merely underfilled. The function of the cap 18 and base 22 vary depending on the direction of delivery of the agent.

In the example of FIG. 6, the mural side of the openings are provided with a cap 18 which is a layer of polymer or other material having an erosion rate which is sufficiently slow to allow substantially all of the therapeutic agent in the therapeutic agent layers 16 to be delivered from the luminal side of the opening prior to complete erosion of the barrier layer. Thus, the cap 18 can provide the luminal delivery. In addition, for mural delivery the cap 18 prevents loss of the beneficial agent during transport, storage, and during the stent implantation procedure. However, the cap layer 18 may be omitted where mural and luminal delivery of the agent is acceptable.

In one example, the cap 18 and/or a base 22 may be formed by a material soluble in a different solvent from the drug matrix 16 to prevent intermixing of layers. For example, where one or more deposits of therapeutic agent and matrix have been deposited in the openings in a solvent, it may be desirable to select a different polymer and solvent combination for the base to prevent the therapeutic agent from mixing into the base. Another region, such as a cap, may be formed by a third non-mixing polymer and solvent combination. In addition to the base and cap, other therapeutic agent layers, protective layers, or separating layers may also be formed of non-mixing polymer/solvent systems in this manner.

For luminal delivery of drug, the base 22 can be provided which serves as a seal during filling of the openings, as well as constraining the contents of the hole 20, 30 at least until the device is implanted. The base 22 is preferably a rapidly degrading biocompatible material for luminal delivery or a slow degrading material for mural delivery.

Since each deposit of both the cap 18 and therapeutic agent 16 is created independently, individual chemical compositions and pharmacokinetic properties can be imparted to each deposit. Numerous useful arrangements of such deposits can be formed, some of which will be described herein. Each of the deposits may include one or more agents in the same or different proportions. Changes in the agent concentration between deposits can be used to achieve a desired delivery profile. The deposits may be solid, porous, or filled with other drugs or excipients.

Figure 2:
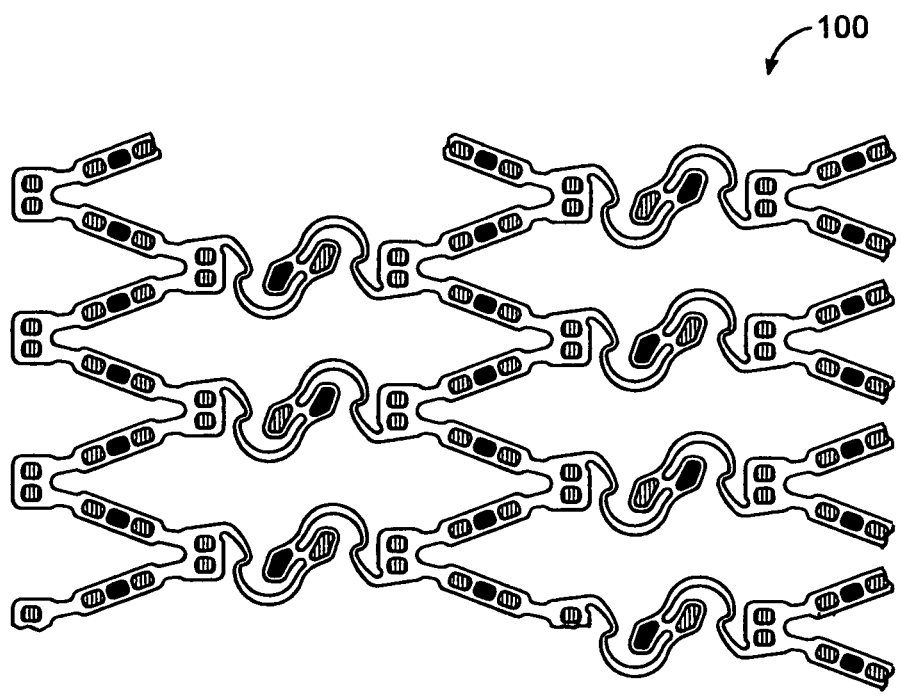
FIG. 2 is an enlarged side view of a portion of an expandable medical device with a majority of the openings loaded with a primary formulation of a therapeutic agent and intermittent openings loaded with a secondary formulation of the therapeutic agent to achieve a combination release kinetic.

FIG. 2 illustrates an alternative exemplary embodiment of an expandable medical device or stent 100 having a plurality of openings in which about 75% of the openings are filled with a first formulation and about 25% of the openings are filled with a second formulation. The present invention is not limited to this specific example, however, and extends to any set of proportions, and does not require that all of the holes include a drug or agent; however, it is clearly advantageous for all of the holes to be filled with a formulation. In particular, when more than two sets of openings having different formulations are provided, as described above, the proportions of the total number of holes that are filled with each formulation can be any number, such that their total is up to 100% of the openings.

Figure 3:
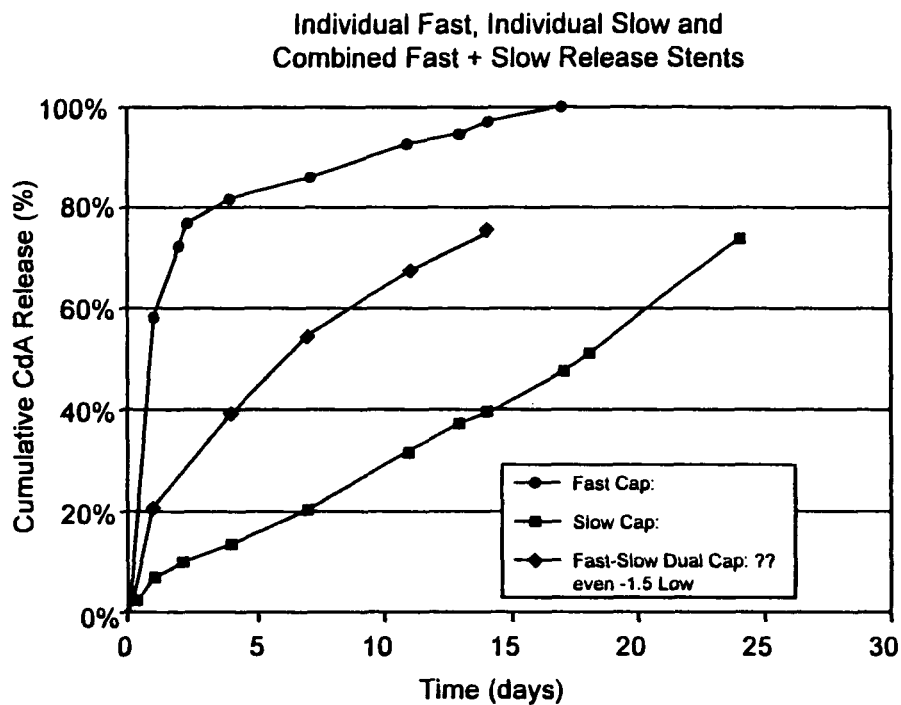
FIG. 3 is a graph of the release rates of three examples of delivery of the drug cladribine (CdA) from stents including 1) a fast release stent having fast release drug formulation in all the openings, 2) a slow release stent having a slow release drug formulation in all the openings, and 3) a medium release stent having alternating openings filled with the fast and slow release drug formulations in the openings.

FIG. 3 shows a graph of the in vitro release kinetics for three examples of stents for delivery of the drug CdA according to a desired release profile. In addition, this drug may be delivered murally for the treatment of restenosis. In the 'fast cap' example (as indicated by ●), 110 μg of CdA was delivered by filling the openings on a stent substantially similar to that illustrated in FIG. 2 as follows: a base of PLA-PCL was first added to the openings to 22% volume; a CdA/PLGA 60/40 mixture was then added to 46% total volume of the openings; and a PLGA cap was added over the drug matrix to 16% total volume of the openings. In the 'slow cap' example (as indicated by ■), 113 μg CdA was delivered by filling the openings on the stent as follows: a base of PEVA was first added to the openings to 27% total volume; a CdA/PLGA 60/40 mixture, with a small amount of Mg(OH)$_2$, was then added to 43% total volume of the openings; and a PLA-PCL cap was added over the drug matrix to 14% total volume of the openings. Finally, in the dual release kinetic example (as indicated by ▲), 147g of CdA was delivered at combined release rates by altering the cap total volume as follows: a base of PEVA was first added to the openings to 25% volume; a CdA/PLGA 60/40 mixture was then added to 44% total volume of the openings; and a PLGA cap was added over the drug matrix to 17% total volume for the 'odd' openings, and a 90% PLA-PCL and 10% PLGA cap was added to 17% total volume of the 'even' openings. The release medium used for these examples was phosphate buffered saline (PBS) and the stents were immersed for selected time periods.

The total drug load (TDL) of CdA from a stent was determined by extracting all the polymer and drug from the stent in a solvent such as DMSO or acetonitrile. The amount of CdA in a solution sample is determined by high pressure liquid chromatography (HPLC) under the following conditions:

Analysis Column: Atlantis (150 mm×4.6 mm 5 micron)
Mobile phase: Acetonitrile/0.020M Sodium Phosphate monobasic/Methanol::7.0% vol./82.0% vol./11.0% vol.
Flow Rate: 1.0 mL/minute
Temperature: 25° C.
Detection wavelength: 260 nm
Injection volume: 10 μL
Retention time: 7 minutes As is shown in the graph of FIG. 3, in the dual release kinetic example, about 20% of the CdA is delivered during the first 24 hours and the remaining CdA is delivered over the following about 15 to about 30 days. The CdA release profile is specifically tailored to the anti-inflammatory action of CdA and would also be useful for other drugs with an anti-inflammatory action. This CdA release is achieved by combining alternating holes of the fast and slow release formulations which are shown on the graph. The combined release is found between the fast and slow releases. The CdA is delivered primarily murally and can be delivered in combination with one or more other drugs either in the same or a different hole.

Figure 4:
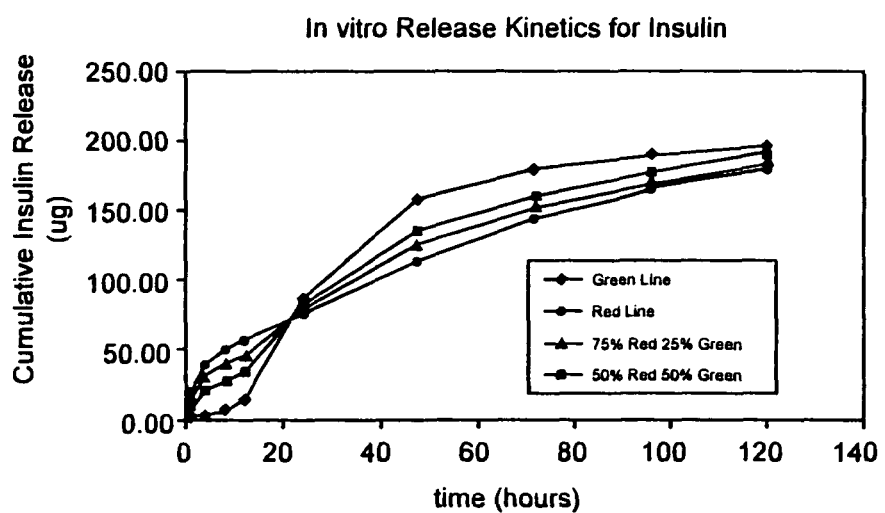
FIG. 4 is a graph of the release rates of four examples of delivery of the drug insulin from stents including 1) a decreasing release stent having decreasing release drug formulation in all the openings, 2) a increasing release stent having an increasing release drug formulation in all the openings, 3) a medium release stent having half of the openings filled with the decreasing and increasing release drug formulations, and 4) a lower medium release stent having 25% of the openings filled with the decreasing release drug formulation and 75% of the openings filled with the increasing release drug formulation.

FIG. 4 shows an example of two theoretical combined release stents for delivery of insulin. Insulin may also be delivered luminally for treatment of Acute Myocardial Infraction (AMI). The graph also shows two actual formulations for releasing insulin from a stent called the "green" and "red" line release curves. In the actual red line example (indicated by the small ■), 202 μg of insulin was delivered by filling the openings on the stent substantially similar to that illustrated in FIG. 2 as follows: a base of PLGA 85/15 was first added to the openings to 28.4% volume; an insulin/PVP 17PF 75/25 mixture was then added to 28.3% total volume of the openings; and 50% of PLGA 85/15 was combined with 50% PLA-PCL 80/20 was added as the cap over the drug matrix to 19.9% total volume of the openings. In the actual green line example (indicated by the ♦), 206 μg of insulin was delivered by filling the openings on the stent substantially similar to that illustrated in FIG. 2 as follows: a base of PLGA 85/15 with PEVA-40 was first added to the openings to 25.2% volume; an insulin/PVP 17PF 75/25 mixture was then added to 29.5% total volume of the openings; and 50% of PLGA 85/15 was combined with 50% PLA-PCL 80/20 and added as the cap over the drug matrix to 31.2% total volume of the openings.

The graph of FIG. 4 also shows the theoretical release curves for a stent with red to green hole ratios of 1:1 and 3:1 (as indicated by the large ■ and ▲, respectively), that is, 50% of the holes filled are for each of red and green configurations, for a ratio of 1:1, while 75% of the holes filled are red configurations and 25% of the holes filled are green configurations, for a ratio of 3:1. It should be understood that any other ratios are also possible. The combined release rates are able to lower the initial release of the red line and even out the late release of the green line. Since the insulin is delivered primarily luminally (into the blood stream) the location of the different formulations or holes 20, 30 in the stent is not critical. Thus, for ease of manufacturing, the first formulation can be positioned in all the holes along one longitudinal side or path along the stent while the other formulation is positioned at another location or side of the stent.

Figure 5:
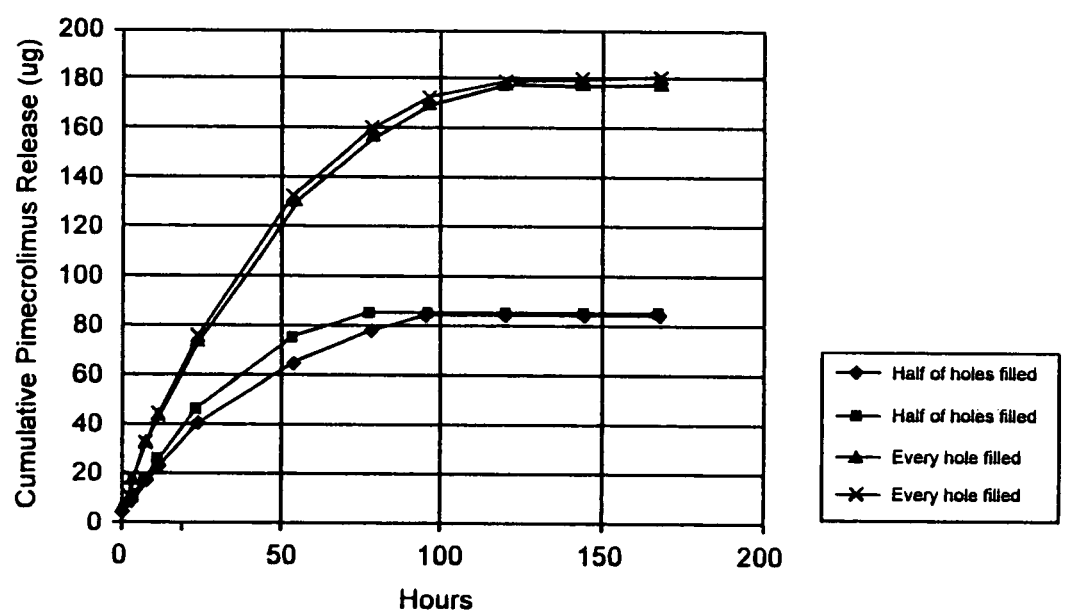
FIG. 5 is a graph of the release rates of examples of delivery of the drug pimecrolimus from stents showing that filling half the number of holes results in half of the release kinetic.

FIG. 5 shows an example of pimecrolimus release from a first pair of stents in which all of the holes are filled (as indicted by the ▲ and x) and a second pair of stents in which 50% of the holes are filled (as indicated by the ■ and ♦), using stents substantially similar to that illustrated in FIG. 2. Pimocrolimus may also be delivered murally for treatment of restenosis. In this example, pimecrolimus was delivered by filling the openings on the stent as follows: a luminal base of PLGA 85/15 (solvent was NMP) was first added to the opening to 22% volume; a pimecrolimus/PLGA 50/50 mixture was added, for 60% of the volume of the drug layer, and a pimecrolimus/PLGA 95/5 mixture was added to make up the remaining 40% volume of the drug layer; the drug layer in total occupies 78% of the volume of the opening. The top curves (the ▲ and x) had a total drug load of 283 µg pimecrolimus and all (100%) of the openings were filled. The bottom curves (the ■ and ♦) had a total drug load of 149 µg pimecrolimus and half (50%) of the openings were filled. The in vitro release experiment was done in 25% ethanol 75% sodium acetate buffer at a pH of 5.

The graph in FIG. 5 demonstrates that half the in vitro release kinetic can be achieved using half the number of holes with the same formulation.

The total drug load (TDL) of pimecrolimus from a stent was determined by extracting all the polymer and drug from the stent in the indicated solvent. The amount of pimecrolimus in a solution sample is determined by high pressure liquid chromatography (HPLC) under the following conditions:

Analysis Column: Chromolith (100 mm×4.6 mm 3 micron RP-E)
Mobile phase: Water/Acetonitrile::68% vol./32% vol.
Flow Rate: 1.5 mL/minute
Temperature: 50° C.
Detection wavelength: 194 nm
Injection volume: 30 µL
Retention time: 15 minutes The release kinetics are determined by placing the stent in a release medium for the selected time periods and measuring the amount of drug released.

Figure 7:
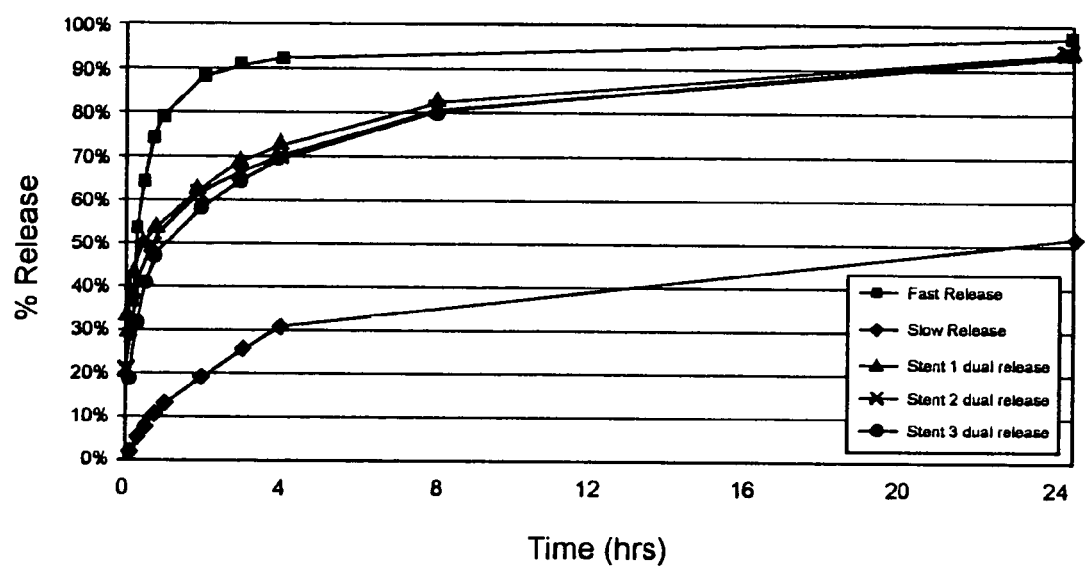
FIG. 7 is a graph of the release rates of examples of delivery of the drug adenosine from stents showing that filling the holes with two different formulations results in a combined or dual release kinetic.

FIG. 7 shows an adenosine and pimecrolimus release from a first fast (indicated by the ■) and second slow (as indicated by the ♦) sets of stents in which all of the holes are filled, using stents substantially similar to that illustrated in FIG. 2. In this example, adenosine and pimecrolimus were delivered by filling the openings on the stent as follows: a luminal base of 50% PLGA and 50% PVP (fast release), or PLGA (slow release) was first added to the opening to 22% volume; a drug matrix was then added of adenosine (total drug load 433 µg for the fast release, 498 µg for the slow release), with 80% adenosine with 20% PVP, occupying 64% of the volume of the openings; and a 50%/50% pimecrolimus/PLGA 95/5 mixture was added to 12% total volume of the opening. The in vitro release experiment was done in 25% ethanol 75% sodium acetate buffer at a pH of 5.

FIG. 7 also shows an example of adenosine release from three stents having dual release kinetics provided by combining the fast release and slow release formulations in the same stent. More specifically, 50% of the holes in each stent were filled according to the fast release (indicted by the ■) and 50% of the holes in each were filled according to the slow release (indicated by the ♦). The total drug load of adenosine in both sets of openings was 445 µg. The in vivo experiment was done in This experiment demonstrates the reproducibility of the in vitro release kinetics of adenosine from implantable medical devices of the present invention, obtained from combinations in a single device of different formulations of the same drug in different sets of holes.

The release kinetics (RK) of adenosine from a stent is determined by extracting drug from the stent in a release medium such as phosphate buffered saline (PBS) at selected time intervals and measuring the amount released by HPLC as described below. The total drug load (TDL) of adenosine from a stent is determined by extracting all the polymer and drug from the stent in a solvent such as dimethyl sulfoxide (DMSO) or acetonitrile and measuring the amount of drug in the sample by HPLC. The amount of Adenosine in a solution sample is determined by High Pressure Liquid Chromatography (HPLC). The following conditions are used:

Analysis Column: Phenomenex Synergy_Hydro RP HPLC Column (150 mm×4.6 mm 4 micron particle)
Mobile phase: Water (0.1% glacial acetic acid in water, adjusted to pH 5.0 with 50% NaOH)/Acetonitrile::95% vol./5% vol.
Flow Rate: 1.0 mL/minute
Temperature: 35° C. ambient
Detection wavelength: 259 nm
Injection volume: 10 µL
Retention time: 6.5 minutes The use of the same drug with different release kinetics in different holes in a stent can achieve desired release kinetics without detrimental effects caused by an uneven distribution of drug delivered to the tissue. This is due to the stent design with multiple small holes closely spaced together. The space between the holes having different releases is much smaller than the space between the struts and achieves summation of the drug release without creating substantial 'hot' or 'cold' drug areas.

Therapeutic Agents

The present invention relates to the delivery of drugs, such as anti-restenotic agents, as well as other cytotoxic or cytostatic agents and microtubule stabilizing agents. Although anti-restenotic agents and agents for treating Acute Myocardial Infraction (AMI) have been primarily described herein, the present invention may also be used to deliver other agents alone or in combination with anti-restenotic agents. Some of the therapeutic agents for use with the present invention which may be transmitted primarily luminally, primarily murally, or both and may be delivered alone or in combination include, but are not limited to, antiproliferatives, antithrombins (i.e., thrombolytics), immunosuppressants including sirolimus, antilipid agents, anti-inflammatory agents, antineoplastics, antimetabolites, antiplatelets, angiogenic agents, anti-angiogenic agents, vitamins, antimitotics, metalloproteinase inhibitors, NO donors, nitric oxide release stimulators, anti-sclerosing agents, vasoactive agents, endothelial growth factors, beta blockers, AZ blockers, hormones, statins, insulin growth factors, antioxidants, membrane stabilizing agents, calcium antagonists (i.e., calcium channel antagonists or blockers), retenoids, anti-macrophage substances, antilymphocytes, cyclooxygenase inhibitors, immunomodulatory agents, angiotensin converting enzyme (ACE) inhibitors, anti-leukocytes, anti-lymphocytes, high-density lipoproteins (HDL) and derivatives, cell sensitizers to insulin, prostaglandins and derivatives, anti-TNF compounds, hypertension drugs, cholesterol-lowering drugs, inhibitors of the intrinsic coagulation, anti-hyperlipoproteinemics, protein kinases, anti-sense oligonucleotides, cardio protectants, petidose inhibitors (increase blycolitic metabolism), endothelin receptor agonists, interleukin-6 antagonists, vasodilators, PPAR gamma agonists, , , , and other miscellaneous compounds, alone or in combinations with any therapeutic agent mentioned herein.

Therapeutic agents for use with the present invention may, for example, take the form of small molecules, peptides, lipoproteins, polypeptides, polynucleotides encoding polypeptides, lipids, protein-drugs, protein conjugate drugs, enzymes, oligonucleotides and their derivatives, ribozymes, other genetic material, cells, antisense, oligonucleotides, monoclonal antibodies, platelets, prions, viruses, bacteria, and eukaryotic cells such as endothelial cells, stem cells, monocyte/macrophages or vascular smooth muscle cells, and the like. Such agents can be used alone or in various combinations with one another. For instance, anti-inflammatories may be used in combination with antiproliferatives to mitigate the reaction of tissue to the antiproliferative. The therapeutic agent may also be a pro-drug, which metabolizes into the desired drug when administered to a host. In addition, therapeutic agents may be pre-formulated as microcapsules, microspheres, microbubbles, liposomes, niosomes, emulsions, dispersions or the like before they are incorporated into the therapeutic layer or the matrix. Therapeutic agents may also be radioactive isotopes or agents activated by some other form of energy such as light or ultrasonic energy, or by other circulating molecules that can be systemically administered. Therapeutic agents may perform multiple functions including modulating angiogenesis, restenosis, cell proliferation, thrombosis, platelet aggregation, clotting, and vasodilation.

Anti-restenotics include, without limitation, include vincristine, vinblastine, actinomycin, epothilone, paclitaxel, paclitaxel derivatives (e.g., docetaxel), rapamycin, rapamycin derivatives, everolimus, tacrolimus, ABT-578, and pimecrolimus.

Antiproliferatives include, without limitation, paclitaxel, actinomycin D, rapamycin, everolimus, ABT-578, tacrolimus, cyclosporin, and pimecrolimus.

Antithrombins include, without limitation, heparin, aspirin, sulfinpyrazone, ticlopidine, ABCIXIMAB, eptifibatide, tirofiban HCL, coumarines, plasminogen, $\alpha_2$-antiplasmin, streptokinase, urokinase, bivalirudin, tissue plasminogen activator (t-PA), hirudins, hirulogs, argatroban, hydroxychloroquin, BL-3459, pyridinolcarbamate, Angiomax, and dipyridamole.

Immunosuppressants include, without limitation, cyclosporine, rapamycin and tacrolimus (FK-506), ABT-578, everolimus, etoposide, sirolimus, and mitoxantrone.

Antilipid agents include, without limitation, HMG CoA reductase inhibitors, nicotinic acid, probucol, and fibric acid derivatives (e.g., clofibrate, gemfibrozil, gemfibrozil, fenofibrate, ciprofibrate, and bezafibrate).

Anti-inflammatory agents include, without limitation, pimecrolimus, salicylic acid derivatives (e.g., aspirin, insulin, sodium salicylate, choline magnesium trisalicylate, salsalate, dflunisal, salicylsalicylic acid, sulfasalazine, and olsalazine), para-amino phenol derivatives (e.g., acetaminophen), indole and indene acetic acids (e.g., indomethacin, sulindac, and etodolac), heteroaryl acetic acids (e.g., tolmetin, diclofenac, and ketorolac), arylpropionic acids (e.g., ibuprofen, naproxen, flurbiprofen, ketoprofen, fenoprofen, and oxaprozin), anthranilic acids (e.g., mefenamic acid and meclofenamic acid), enolic acids (e.g., piroxicam, tenoxicam, phenylbutazone and oxyphenthatrazone), alkanones (e.g., nabumetone), glucocorticoids (e.g., dexamethaxone, prednisolone, and triamcinolone), pirfenidone, and tranilast.

Anti-metabolics include, withour limitation, chlorodeoxy adenosine (2-CdA or cladribine).

Antineoplastics include, without limitation, nitrogen mustards (e.g., mechlorethamine, cyclophosphamide, ifosfamide, melphalan, and chlorambucil), methylnitrosoureas (e.g., streptozocin), 2-chloroethylnitrosoureas (e.g., carmustine, lomustine, semustine, and chlorozotocin), alkanesulfonic acids (e.g., busulfan), ethylenimines and methylmelamines (e.g., triethylenemelamine, thiotepa and altretamine), triazines (e.g., dacarbazine), folic acid analogs (e.g., methotrexate), pyrimidine analogs (5-fluorouracil, 5-fluorodeoxyuridine, 5-fluorodeoxyuridine monophosphate, cytosine arabinoside, 5-azacytidine, and 2',2'-difluorodeoxycytidine), purine analogs (e.g., mercaptopurine, thioguanine, azathioprine, adenosine, pentostatin, cladribine, and erythrohydroxynonyladenine), antimitotic drugs (e.g., vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin), phenoxodiol, etoposide, and platinum coordination complexes (e.g., cisplatin and carboplatin).

Antiplatelets include, without limitation, insulin, dipyridamole, tirofiban, eptifibatide, abciximab, and ticlopidine.

Angiogenic agents include, without limitation, phospholipids, ceramides, cerebrosides, neutral lipids, triglycerides, diglycerides, monoglycerides lecithin, sphingosides, angiotensin fragments, nicotine, pyruvate thiolesters, glycerol-pyruvate esters, dihydoxyacetone-pyruvate esters and monobutyrin.

Anti-angiogenic agents include, without limitation, endostatin, angiostatin, fumagillin and ovalicin.

Vitamins include, without limitation, water-soluble vitamins (e.g., thiamin, nicotinic acid, pyridoxine, and ascorbic acid) and fat-soluble vitamins (e.g., retinal, retinoic acid, retinaldehyde, phytonadione, menaqinone, menadione, and alpha tocopherol).

Antimitotics include, without limitation, vinblastine, vincristine, vindesine, vinorelbine, paclitaxel, docetaxel, epipodophyllotoxins, dactinomycin, daunorubicin, doxorubicin, idarubicin, epirubicin, mitoxantrone, bleomycins, plicamycin and mitomycin.

Metalloproteinase inhibitors include, without limitation, TIMP-1, TIMP-2, TIMP-3, and SmaPI.

NO donors include, without limitation, L-arginine, amyl nitrite, glyceryl trinitrate, sodium nitroprusside, molsidomine, diazeniumdiolates, S-nitrosothiols, and mesoionic oxatriazole derivatives.

NO release stimulators include, without limitation, adenosine.

Anti-sclerosing agents include, without limitation, collagenases and halofuginone.

Vasoactive agents include, without limitation, nitric oxide, adenosine, nitroglycerine, sodium nitroprusside, hydralazine, phentolamine, methoxamine, metaraminol, ephedrine, trapadil, dipyridamole, vasoactive intestinal polypeptides (VIP), arginine, and vasopressin.

Endothelial growth factors include, without limitation, VEGF (Vascular Endothelial Growth Factor) including VEGF-121 and VEG-165, FGF (Fibroblast Growth Factor) including FGF-1 and FGF-2, HGF (Hepatocyte Growth Factor), and Ang1 (Angiopoietin 1).

Beta blockers include, without limitation, propranolol, nadolol, timolol, pindolol, labetalol, metoprolol, atenolol, esmolol, and acebutolol.

Hormones include, without limitation, progestin, insulin, the estrogens and estradiols (e.g., estradiol, estradiol valerate, estradiol cypionate, ethinyl estradiol, mestranol, quinestrol, estrond, estrone sulfate, and equilin).

Statins include, without limitation, mevastatin, lovastatin, simvastatin, pravastatin, atorvastatin, and fluvastatin.

Insulin growth factors include, without limitation, IGF-1 and IGF-2.

Antioxidants include, without limitation, vitamin A, carotenoids and vitamin E.

Membrane stabilizing agents include, without limitation, certain beta blockers such as propranolol, acebutolol, labetalol, oxprenolol, pindolol and alprenolol.

Calcium antagonists include, without limitation, amlodipine, bepridil, diltiazem, felodipine, isradipine, nicardipine, nifedipine, nimodipine and verapamil.

Retinoids include, without limitation, all-trans-retinol, all-trans-14-hydroxyretroretinol, all-trans-retinaldehyde, all-trans-retinoic acid, all-trans-3,4-didehydroretinoic acid, 9-cis-retinoic acid, 11-cis-retinal, 13-cis-retinal, and 13-cis-retinoic acid.

Anti-macrophage substances include, without limitation, NO donors.

Anti-leukocytes include, without limitation, 2-CdA, IL-1 inhibitors, anti-CD116/CD18 monoclonal antibodies, monoclonal antibodies to VCAM, monoclonal antibodies to ICAM, and zinc protoporphyrin.

Cyclooxygenase inhibitors include, without limitation, Cox-1 inhibitors and Cox-2 inhibitors (e.g., CELEBREX® and VIOXX®).

Immunomodulatory agents include, without limitation, immunosuppressants (see above) and immunostimulants (e.g., levamisole, isoprinosine, Interferon alpha, and Interleukin-2).

ACE inhibitors include, without limitation, benazepril, captopril, enalapril, fosinopril sodium, lisinopril, quinapril, ramipril, spirapril, and 2B3 ACE inhibitors.

Cell sensitizers to insulin include, without limitation, glitazones, P PAR agonists and metformin.

Antisense oligonucleotides include, without limitation, resten-NG.

Cardio protectants include, without limitation, VIP, pituitary adenylate cyclase-activating peptide (PACAP), apoA-I milano, amlodipine, nicorandil, cilostaxone, insulin, adenosine, and thienopyridine.

Petidose inhibitors include, without limitation, omnipatrilat.

PPAR gamma agonists include, without limitation, farglitizar, rosiglitazone, muraglitazar, pioglitazone, troglitazone, and balaglitazone.

Miscellaneous compounds include, without limitation, Adiponectin.

Agents may also be delivered using a gene therapy-based approach in combination with an expandable medical device. Gene therapy refers to the delivery of exogenous genes to a cell or tissue, thereby causing target cells to express the exogenous gene product. Genes are typically delivered by either mechanical or vector-mediated methods.

Some of the agents described herein may be combined with additives which preserve their activity. For example additives including surfactants, antacids, antioxidants, and detergents may be used to minimize denaturation and aggregation of a protein drug. Anionic, cationic, or nonionic detergents may be used. Examples of nonionic additives include but are not limited to sugars including sorbitol, sucrose, trehalose; dextrans including dextran, carboxy methyl (CM) dextran, diethylamino ethyl (DEAE) dextran; sugar derivatives including D-glucosaminic acid, and D-glucose diethyl mercaptal; synthetic polyethers including polyethylene glycol (PEF and PEO) and polyvinyl pyrrolidone (PVP); carboxylic acids including D-lactic acid, glycolic acid, and propionic acid; detergents with affinity for hydrophobic interfaces including n-dodecyl-β-D-maltoside, n-octyl-β-D-glucoside, PEO-fatty acid esters (e.g. stearate (myrj 59) or oleate), PEO-sorbitan-fatty acid esters (e.g. Tween 80, PEO-20 sorbitan monooleate), sorbitan-fatty acid esters (e.g. SPAN 60, sorbitan monostearate), PEO-glyceryl-fatty acid esters; glyceryl fatty acid esters (e.g. glyceryl monostearate), PEO-hydrocarbon-ethers (e.g. PEO-10 oleyl ether; triton X-100; and Lubrol. Examples of ionic detergents include but are not limited to fatty acid salts including calcium stearate, magnesium stearate, and zinc stearate; phospholipids including lecithin and phosphatidyl choline; CM-PEG; cholic acid; sodium dodecyl sulfate (SDS); docusate (AOT); and taumocholic acid.

While the invention has been described in detail with reference to exemplary embodiments thereof, it will be apparent to one skilled in the art that various changes can be made, and equivalents employed, without departing from the scope of the invention. The foregoing description of the exemplary embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

The invention claimed is:

1. A medical device for delivery of a therapeutic agent with a combined release profile, the device comprising:
   an implantable body, wherein the implantable body includes an expandable stent that has a plurality of struts;
   one or more first through-openings formed in the plurality of struts containing a first beneficial agent for delivery to tissue, wherein the first beneficial agent comprises a therapeutic agent and a first matrix, wherein the therapeutic agent and the first matrix are arranged to deliver the therapeutic agent from the one or more first through-openings according to a first release curve; and
   one or more second through-openings formed in the plurality of struts containing a second beneficial agent for delivery to tissue, wherein the second beneficial agent comprises the therapeutic agent and a second matrix, wherein the therapeutic agent and the second matrix are arranged to deliver the therapeutic agent from the one or more second through-openings according to a second release curve which is different from the first release curve;
   wherein the one or more first through-openings are alternatively arranged relative to the one or more second through-openings along each of the plurality of struts, and the one or more first through-openings are alternatively arranged relative to the one or more second through-openings along a circumferential direction of the implantable body, and in each occurrence of the alternatively arranged one or more first through-openings and the respective one or more second through-openings, a number of openings in the one or more first through-openings and a number of openings in the one or more second through-openings are present in a ratio, wherein the plurality of struts include:
a first circumferential row of struts connected to each other in a zig-zag arrangement,
a second circumferential row of struts connected to each other in a zig-zag arrangement, and
a third circumferential row of struts, each strut of the third circumferential row of struts extends in a longitudinal direction of the implantable body, each strut of the third circumferential row of struts connects a strut of the first circumferential row of struts and a strut of the second circumferential row of struts,
wherein the one or more first through-openings are alternatively arranged relative to the one or more second through-openings along each strut of the third circumferential row of struts, and the one or more first through-openings are alternatively arranged relative to the one or more second through-openings on the third circumferential row of struts in the circumferential direction.

2. The medical device according to claim 1, wherein the first release curve has an administration period of less than ½ an administration period of the second release curve.

3. The medical device according to claim 1, wherein the first release curve has a maximum release rate of at least 2 times a maximum release rate of the second release curve.

4. The medical device according to claim 3, wherein the first release curve is a burst release in which at least 80 percent of the agent is released over an administration period of 5 days or less and the second release curve is characterized as a substantially constant release which extends over an administration period of at least 2 weeks.

5. The medical device according to claim 1, wherein the one or more first through-openings and the one or more second through-openings together create a combination release kinetic having an initial release of about 40-60 percent of a total drug loaded in the medical device over about 2-4 days and a substantially constant release of about 40-60 percent of the total drug load over the following 10-60 days.

6. The medical device according to claim 1, wherein the therapeutic agent is insulin.

7. The medical device according to claim 1, wherein the therapeutic agent is pimecrolimus.

8. The medical device according to claim 1, wherein the therapeutic agent is paclitaxel.

9. The medical device according to claim 1, wherein the therapeutic agent is adenosine.

10. The medical device according to claim 1, wherein the therapeutic agent is an agent for treating restenosis.

11. The medical device according to claim 1, further comprising:
one or more third through-openings formed in the implantable body containing a third beneficial agent for delivery to tissue, wherein the third beneficial agent comprises the therapeutic agent and a third matrix, wherein the therapeutic agent and third matrix are arranged to deliver the therapeutic agent from the one or more third through-openings according to a third release curve which is different from the first release curve and the second release curve.

12. The medical device according to claim 1, wherein the one or more first through-openings and the one or more second through-openings are laser cut.

13. The medical device according to claim 1, wherein the one or more first through-openings and the one or more second through-openings are on different portions of the medical device.

14. The medical device according to claim 1, wherein the first and second beneficial agents are configured and arranged to be delivered in overlapping administration periods.

15. The medical device of claim 1, wherein a space between one of the one or more first through-openings and one of the one or more second through-openings located next to the one or more first through-openings is smaller than a space between two neighboring struts of the plurality of struts.

16. The medical device of claim 1, wherein the first matrix and the second matrix comprise biodegradable polymers, the first matrix and the second matrix comprise the same material in different molecular weights or combinations of molecular weights, the first beneficial agent further includes a first barrier layer at one side of the one or more first through-openings for directional delivery of the first beneficial agent and the second beneficial agent includes a second barrier layer at one side of the one or more second through-openings for directional delivery of the second beneficial agent.

17. The medical device according to claim 16, wherein the first and second barrier layers are the same and the first and second beneficial agents are delivered to a same side of the medical device.

18. The medical device according to claim 16, wherein the first beneficial agent further includes a first cap comprising a degradable material in the one or more first through-openings, and the first cap is located at the primary delivery side of the one or more first through-openings, opposite the first barrier layer, and
wherein the second beneficial agent includes a second cap comprising a degradable material in the one or more second through-openings, and the second cap is located at the primary delivery side of the one or more second through-openings, opposite the second barrier layer.

* * * * *